United States Patent [19]

Martin

[11] Patent Number: 5,575,817
[45] Date of Patent: Nov. 19, 1996

[54] AORTO FEMORAL BIFURCATION GRAFT AND METHOD OF IMPLANTATION

[76] Inventor: Eric C. Martin, 134 Old Post Rd. North, Croton on Hudson, N.Y. 10520

[21] Appl. No.: 293,541

[22] Filed: Aug. 19, 1994

[51] Int. Cl.⁶ ......................................................... A61F 2/06
[52] U.S. Cl. ................................................. 623/1; 623/12
[58] Field of Search .................................... 623/1, 11, 12; 606/191, 198

[56] References Cited

U.S. PATENT DOCUMENTS

| | | |
|---|---|---|
| 3,657,744 | 4/1972 | Ersek . |
| 4,140,126 | 2/1979 | Choudhury . |
| 4,512,338 | 4/1985 | Balko et al. . |
| 4,577,631 | 3/1986 | Kreamer . |
| 4,787,899 | 11/1988 | Lazarus ........................................ 623/1 |
| 5,104,399 | 4/1992 | Lazarus ........................................ 623/1 |
| 5,316,023 | 5/1994 | Palmaz et al. ........................... 128/898 |
| 5,383,926 | 1/1995 | Lock et al. .................................. 623/1 |
| 5,387,235 | 2/1995 | Chuter ......................................... 623/1 |

*Primary Examiner*—Michael J. Milano
*Attorney, Agent, or Firm*—Fulbright & Jaworski L.L.P.

[57] ABSTRACT

An apparatus and method for reinforcing a bifurcating blood vessel. The apparatus comprises two sections that form an inverted Y-shape graft prosthesis when joined together inside the blood vessel. The method comprises inserting the two sections into the bifurcating blood vessel by encasing the sections in retractable membranes mounted on two catheters, inserting the catheters into the blood vessel, deploying and attaching the first section to the vessel, deploying the second section and joining it to the first section.

17 Claims, 3 Drawing Sheets

AORTO FEMORAL BIFURCATION GRAFT AND METHOD OF IMPLANTATION

BACKGROUND OF THE INVENTION

1. Field of the Invention

This invention relates to a graft prosthesis for placement within a bifurcating blood vessel, such as the lower abdominal aorta, without the requirement for open surgery.

2. Description of the Related Technology

Blood vessels, particularly the lower abdominal aorta and the iliac vessels, are subject to aneurysm formation and severe atherosclerotic disease which leads to multiple stenoses. Traditionally, two methods have been used to repair blood vessels damaged by these afflictions. Both methods involve the use of a graft prosthesis.

In the majority of instances a hollow bifurcation graft, shaped in the form of an inverted Y, is used to bypass the diseased portion of the blood vessel. This involves open surgery in which the upper limb of the inverted Y is sutured to the aorta immediately below the renal arteries, and the lower limbs of the inverted Y are sutured to the corresponding iliac arteries. Unfortunately, this method carries a significant mortality rate due to the poor health of the patient and the risks posed by anesthesia.

In other instances, a hollow tube graft is inserted by catheter into the aorta. The tube is positioned within the aorta by fluoroscopic control and is fastened in place at each end by hooks or barbed stents that anchor into the walls of the aorta. This method, however, is of limited utility, since in the majority of cases the blood vessel damage extends to the iliac arteries, requiring an inverted Y graft for repair.

SUMMARY OF THE INVENTION

It is an object of the present invention to provide a novel inverted Y graft prosthesis. It is a further object of the invention to provide a method for placing said novel inverted Y graft prosthesis in a patient without open surgery. It is a further object of the invention to provide a method for placing said novel inverted Y graft prosthesis by a catheter. Thus, the disadvantages in the prior art are overcome. According to the invention, an inverted Y graft is provided which is comprised of two sections. The first section of the inverted Y graft is comprised of the upper limb, the first lower limb, and a partial length of the second lower limb of the inverted Y. The second section of the inverted Y graft is comprised of the remainder of the second lower limb of the inverted Y. The inverted Y graft according to the invention may be placed in a patient in two consecutive stages, each stage requiring the insertion by catheter of a segment of the inverted Y graft. Prior to the initiation of the two stages, the length and diameter of the neck of the aneurysm, the aortic diameter, the length of the aorta from the renal arteries to the bifurcation, and the length of the common iliac arteries are measured by angiography or some other appropriate imaging study. These measurements are used to determine the appropriate dimensions of the inverted Y graft. The first stage of the method according to the invention involves the insertion and placement within the blood vessel of the first section of the graft. The second stage of the method according to the invention involves the insertion and attachment of the second section of the graft to the first section. Once the second section is attached to the first section, the inverted Y is complete.

The first stage of the method according to the invention is performed from the more favorable iliac system for primary access. This is usually the vessel which is the least torturous and the least diseased. The first section of the inverted Y graft, encased within a retractable membrane, is mounted on the head of a catheter. The catheter is introduced into the iliac artery through a vascular sheath or surgical cut and is advanced into the aorta. Under anglographic and fluoroscopic control, the catheter is positioned immediately below the renal arteries. By partially withdrawing the retractable membrane, the upper limb of the inverted Y is released. As it releases, it expands and fastens to the walls of the aorta by barbs, hooks, or some other means. The remaining portion of the first section is then released into the aorta and the first iliac artery by fully withdrawing the retractable membrane. The catheter is then removed.

The second stage of the method according to the invention is performed from the contralateral side of the body. A second catheter, having a retractable membrane containing the second section of the inverted Y graft, is introduced into the iliac artery from the contralateral side of the body and advanced into the aorta. Under fluoroscopic control, the catheter is positioned inside the partial lower limb of the inverted Y of the deployed first section. By partially withdrawing the retractable membrane, the second section of the inverted Y is released and expands to form a fit, which may be reinforced with barbs or hooks, with the first section of the inverted Y. The inverted Y is thereby completed. By fully withdrawing the membrane and catheter, the second lower limb is positioned inside the second iliac artery.

The completion of the two stage procedure results in the insertion of the inverted Y graft with the upper limb anchored to the aorta above the aneurysm and the lower limbs positioned in the corresponding iliac arteries.

Another object of the present invention is to provide support to the inverted Y graft in order to prevent it from kinking or twisting once deployed. This is accomplished by bonding the graft to the inside of a self-expanding, mesh support tailored to the same measurements. The support may be a stent or a similar structure. Once the inverted Y graft is deployed, the mesh provides the graft with the necessary support to prevent it from kinking or twisting.

Another object of the present invention is to prevent the formation of thrombi that may result from the prolonged exposure of blood to any metallic surface. This is accomplished by covering the mesh support with a suitable non-metallic material.

DESCRIPTION OF THE PREFERRED EMBODIMENTS OF THE INVENTION

Figure 1:
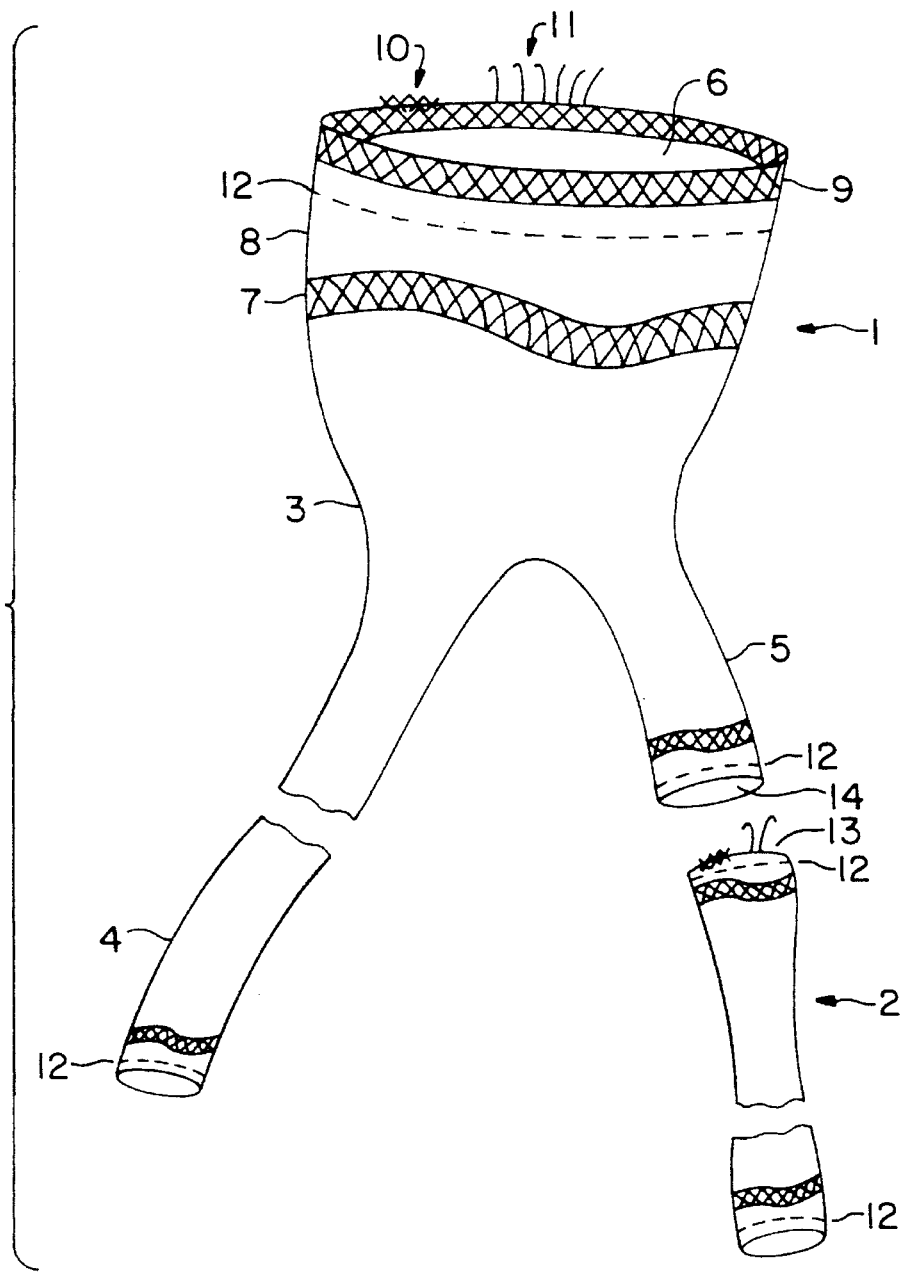
FIG. 1 shows the preferred embodiment of the inverted Y graft prosthesis according to the invention.

The preferred embodiment of the present invention is illustrated in FIG. 1. The object of the invention is realized upon the insertion and union of the first section i with the second section 2 to form an inverted Y-shape graft in the bifurcating lumen. The first section 1 comprises a hollow, bifurcation graft 3 made of a suitable material. Examples of suitable materials include, but are not limited to, thin walled dacron or thin walled polytetrafluorethaline (PTFE). The first lower limb 4 of the inverted Y graft is cut at an appropriate length, normally 8–18 cm, as determined by the angiography or anatomy of the individual patient. The partial length of the second lower limb 5 is approximately 2–4 cm. The upper limb 6 of the inverted Y graft is approximately 15–35 mm in diameter and approximately 4–8 cm in length. The whole of this first section is bonded and attached to the inside of a compressible expanding mesh support 7. The support may be a stent or a similar structure. The mesh support 7 may be of a medical grade, super alloy, stainless steel and may be entirely covered by a non-metallic material 8. It extends approximately 1 cm beyond the material of the upper limb 6. This extension 9 accommodates some fastener means such as barbs 10 or outward-facing hooks 11 to fasten it to the inside of the lumen. The line of attachment of the section to the support may be marked with fine platinum wire 12 for heightened fluoroscopic visibility.

The second section 2 comprises a hollow tube graft which may be of the same material as the first section. It is bonded to the inside of an expanding mesh support of the same dimensions. The length of this section is such that when it forms a complete inverted Y with the first section, the completed second lower limb is of an appropriate length as determined by the angiography of the patient. The upper end 13 of the second section 2 is slightly larger in diameter than the corresponding diameter 14 of the partial length of the second lower limb 5 of the first section 1. This allows for a friction fit of the two sections when the second section 2 expands within the first section 1. Alternatively or in conjunction with this friction fit, the upper end 13 may include a fastener means such as barbs, outward-facing hooks, or some other means of attachment. The upper and lower ends of the second section 2 may be traced with platinum wire 12 in order to enhance their fluoroscopic visibility.

Figure 2:
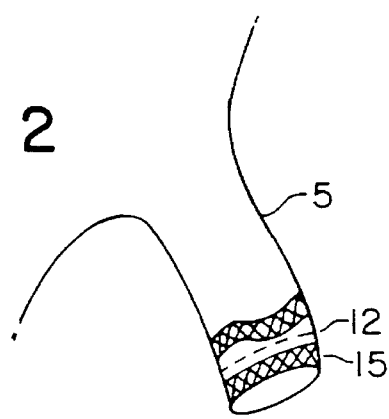
FIG. 2 shows a second embodiment of the short limb of the first section of the inverted Y graft prosthesis according to the invention.

An alternative embodiment of the partial length of the second lower limb 5 of the first section is illustrated in FIG. 2. In this embodiment the expanding mesh support 15 extends past the covering material of the partial length of the second lower limb 5 of the first section.

Figure 3:
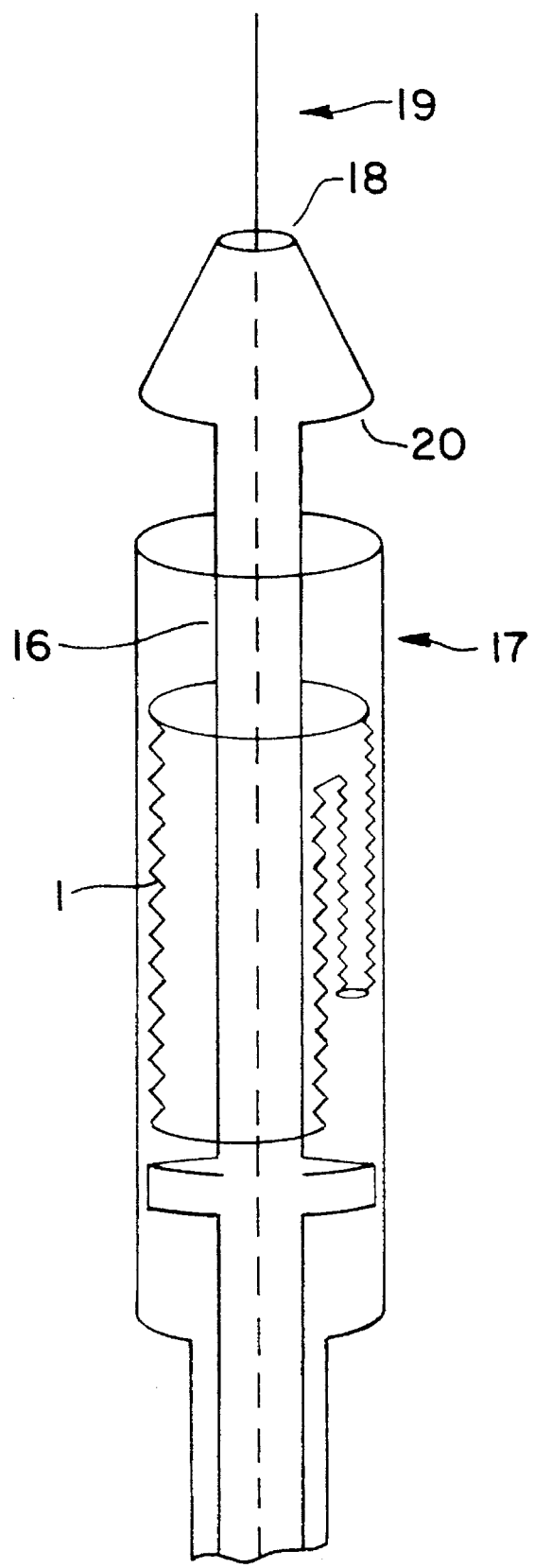
FIG. 3 shows a catheter having a retractable membrane containing the first section of the inverted Y graft prosthesis according to the invention.

The mounting of the first section on a catheter is illustrated in FIG. 3. The first section 1 is compressed and then mounted in such a way that the catheter 16 passes through the first lower limb 4 and the upper limb 6 of the first section. The first section, including the partial length of the second lower limb, is encased and held in its compressed state by a retractable membrane 17. The leading edge 18 of the catheter 16 is tapered to such a diameter that it allows a guide wire 19 to pass through it. The trailing edge 20 is recessed for the section when it is collapsed onto the catheter and retained by the retaining membrane. A luer-lok hub is located on the trailing edge of the catheter. The mounting of the second section 2 of the graft is performed on a catheter in a similar fashion.

Figure 4:
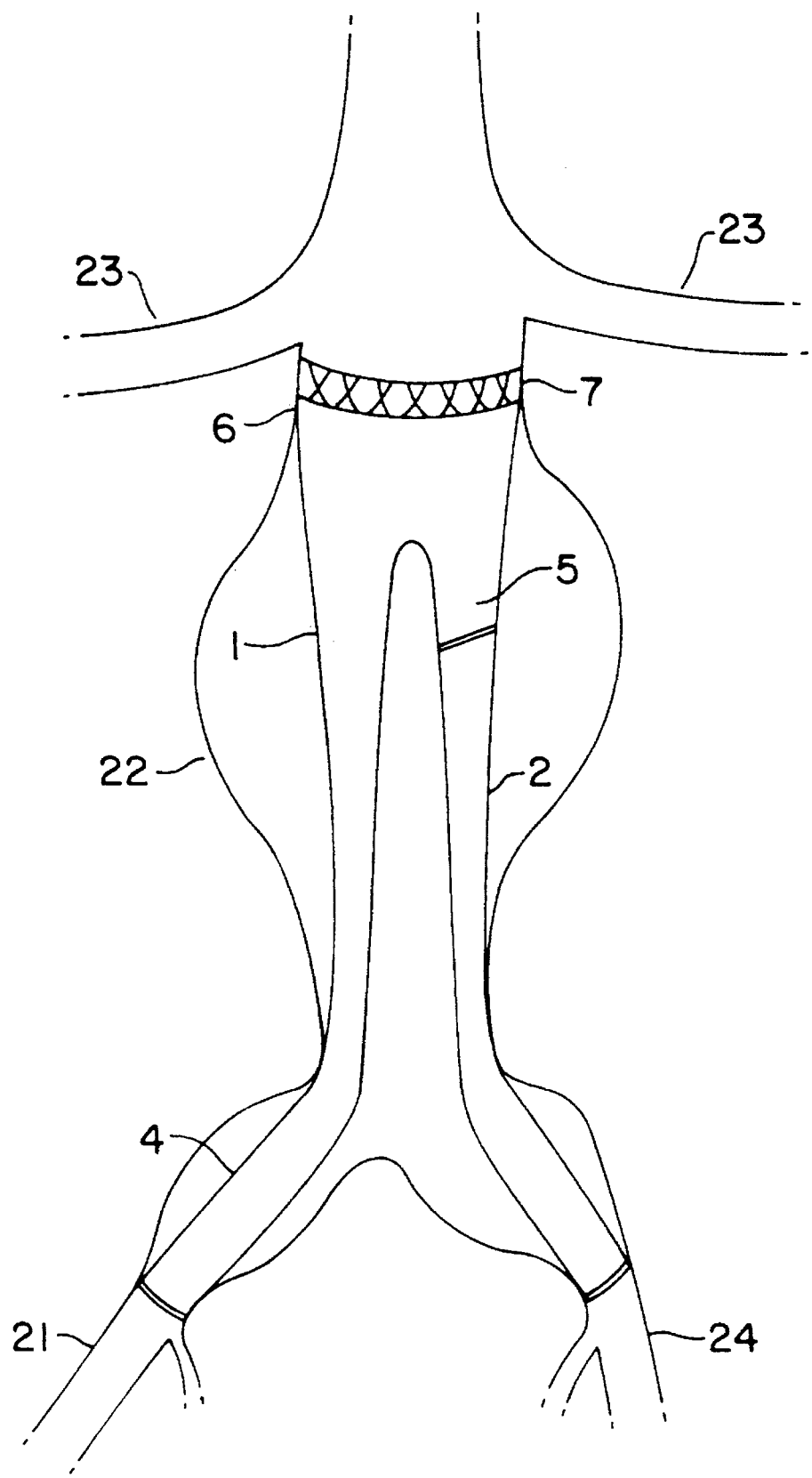
FIG. 4 shows the inverted Y graft prosthesis fully positioned within the aorta according to the invention.

The fully inserted and positioned inverted Y graft is illustrated in FIG. 4. To achieve this state, the most favorable iliac system 21 is chosen for primary access. This is usually the vessel which is least torturous and the least diseased. Primary access is accomplished through a surgical cut or through a vascular sheath. A second smaller sheath may be introduced percutaneously through the contralateral side into the femoral artery and a 5 French catheter may be introduced through the sheath and positioned above the renal arteries for anglographic control of the procedure. Referring to both FIG. 3 and FIG. 4, a guide wire 19 is introduced through the primary access site and advanced into the aorta 22. Under angiographic and fluoroscopic control, the catheter on which the first section is mounted is introduced into the aorta 22 and positioned immediately below the renal arteries 23. The upper limb 6 of the first section of the inverted Y is deployed by partially withdrawing the retaining membrane 17 that retains the compressed first section. As it deploys, the upper limb expands and fastens to the wall of the aorta under the force of the expandable mesh 7. The fastening means may be barbs, hooks, or some other means. The first section of the graft 1 is then fully deployed as the retaining membrane 17 is fully withdrawn. The catheter is removed through the iliac artery 21. The first lower limb 4 of the inverted Y is thus positioned in the iliac artery. The second section 2 is similarly introduced through the contralateral iliac artery 24. Under fluoroscopic and anglographic control, the second section catheter is positioned so that its upper end 13 is inside the partial length of the second lower limb 5 of the first section 1. The retaining membrane is then partially withdrawn and the upper end 13 of the second section is deployed. As it deploys, the second section expands under the force of the expandable mesh and fastens to the inside of the first section. The fastening means may be barbs, hooks, or some other means.

The second section 2 of the graft is then fully deployed as the retaining membrane is fully withdrawn. The catheter is then removed through the iliac artery 24. The second lower limb of the inverted Y is thus positioned in the iliac artery 24, and the inverted Y graft is completed.

I claim:

1. An apparatus for reinforcing a bifurcated lumen comprising:
    a first section, configured to be positioned within the lumen, comprising:
        an upper limb, configured to fit within the lumen upstream of the bifurcation;
        a first lower limb, configured to extend into a first leg of said bifurcation when said first section is positioned in the lumen, and
        a second lower limb, shorter than said first lower limb, and configured so that when said first section is positioned in the lumen, said second lower limb does not extend into a second leg of said bifurcation.

2. The apparatus of claim 1, further comprising a second section configured to be positioned separately within the lumen and joined to said second lower limb of the first section, effectively extending said second lower limb into said second leg of said bifurcation.

3. The apparatus of claim 2, wherein the first section and the second section form an inverted Y-shape when joined.

4. The apparatus of claim 3, wherein the first and second sections each comprise a graft attached to a support.

5. The apparatus of claim 4, wherein the support comprises a compressible and expandable mesh.

6. The apparatus of claim 4, further comprising a non-metallic material covering the support.

7. The apparatus of claim 4, wherein the graft is made of a material selected from the group consisting of dacron and PTFE.

8. The apparatus of claim 4, wherein the support comprises a metallic mesh.

9. The apparatus of claim 4, further comprising a platinum wire situated at a line of attachment between the graft and the support.

10. The apparatus of claim 4, wherein the support extends beyond the graft.

11. The apparatus of claim 4, further comprising a fastener attached to the support.

12. The apparatus of claim 11, wherein the fastener is selected from the group consisting of barbs and hooks.

13. The apparatus of claim 3, wherein the second section is a tube graft.

14. The apparatus of claim 3, further comprising a fastener on one of the sections.

15. The apparatus of claim 14, wherein the fastener is selected from the group consisting of barbs and hooks.

16. The apparatus of claim 3, wherein the lengths of the lower limbs of the inverted Y-shape are 8–18 cm, and the length of the upper limb of the inverted Y-shape is 4–8 cm.

17. The apparatus of claim 3, wherein the diameters of the lower limbs of the inverted Y-shape are 8–12 mm, and the diameter of the upper limb of the inverted Y-shape is 15–35 mm.

* * * * *

Adverse Decision In Interference

Patent No. 5,575,817, Eric C. Martin, AORTO FEMORAL BIFURCATION GRAFT AND METHOD OF IMPLANTATION, Interference No. 104,192, final judgment adverse to the patentee rendered July 27, 2001, as to claims 2-17.

*(Official Gazette October 30, 2001)*